United States Patent [19]

Sergienko et al.

[11] Patent Number: 4,778,464
[45] Date of Patent: Oct. 18, 1988

[54] INTRAOCULAR PROSTHETIC LENS

[75] Inventors: Nikolai M. Sergienko; Zoya F. Veselovskaya, both of Kiev, U.S.S.R.

[73] Assignee: Kievsky Gosudarstvenny Institut Usovershenstvovania Vrachei, Kiev, U.S.S.R.

[21] Appl. No.: 35,893

[22] Filed: Apr. 8, 1987

[51] Int. Cl.$^4$ .................................................. A61F 2/16
[52] U.S. Cl. ...................................................... 623/6
[58] Field of Search ............................................ 623/6

[56] References Cited

U.S. PATENT DOCUMENTS

| 3,866,249 | 2/1975 | Flom | 623/6 |
| 3,906,551 | 9/1975 | Otter | 623/6 |
| 4,073,015 | 2/1978 | Peyman et al. | 623/6 |
| 4,079,470 | 3/1978 | Deeg et al. | 623/6 |

FOREIGN PATENT DOCUMENTS

| WO86/01096 | 2/1986 | PCT Int'l Appl. | 623/6 |
| 563174 | 7/1977 | U.S.S.R. | 623/6 |
| 1116571 | 5/1985 | U.S.S.R. | 623/6 |

Primary Examiner—Ronald L. Frinks
Attorney, Agent, or Firm—Fleit, Jacobson, Cohn & Price

[57] ABSTRACT

An intraocular prosthetic lens, comprising an optical lens, a first loop-shaped supporting element, a second supporting element made up of two rods which diverge, past a first bend thereon, so as to face the posterior lens surface, and past a second bend thereon are directed with their ends towards each other, and a third supporting element made up of two rods which are located on the side of the loop-shaped supporting element on the same lens surface with the second supporting element. Each of the rods of the third supporting element has a bend past which the rods diverge from each other and are arranged parallel to the lens plane and to the loop-shaped supporting element, said bend being spaced apart from the anterior lens surface a distance 1.5 to 2 times the lens thickness on the portion where the third supporting element is secured.

1 Claim, 2 Drawing Sheets

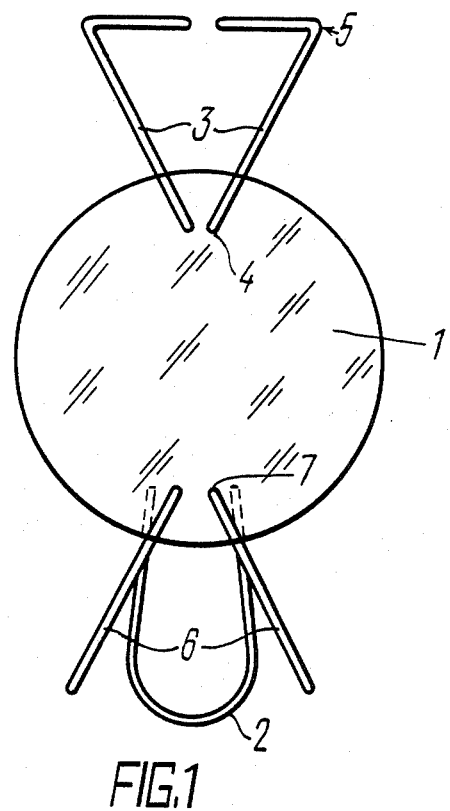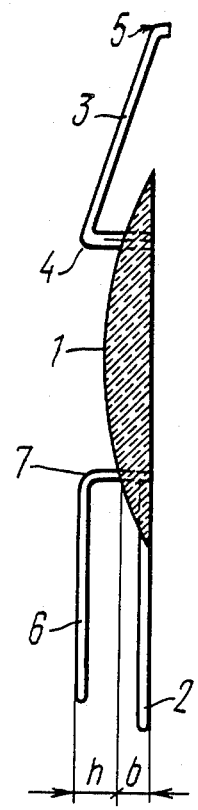
FIG.1
FIG.2

INTRAOCULAR PROSTHETIC LENS

FIELD OF THE INVENTION

The invention relates to medical prosthetic devices and is particularly concerned with intraocular prosthetic lenses.

The invention is applicable for implanting an intraocular lens in an eye after cataract extraction.

PRIOR ART

Known in the present state of the art is an intraocular prosthetic lens, comprising an optical lens and supporting elements made as two loops of a platinum wire (cf. USSR Inventor's Certificate No. 563,174, Int.Cl. A61B 1/16, 1973).

The aforementioned known intraocular lens is disadvantageous in that the loop-shaped supporting elements fail to fix the lens by themselves; that is why the implantation technique provides for application of a suture aimed at holding the top loop to the iris. Besides, the heretofore-known intraocular lens features such a construction arrangement that exhibits the optical lens coplanar with the supporting elements. With the intraocular lens having an overall length of 9 of 10 mm, to insert it in the posterior eye chamber by gaining access through the pupillary orifice is too a hard task from the standpoint of operative technique. That is why the known intraocular lens is to be introduced into the posterior eye chamber through an incision in the iris, which involves an additional injury to the latter and a necessity of suturing the operative iridal wound.

One more prior-art intraocular lens is known to comprise an optical lens and supporting elements whose characteristic feature resides in that one of said supporting elements is loop-shaped, while the other is made up of two rods, each having two bends or flexures. The first of said bends is provided at a distance from the optical lens anterior surface 1.5 times the lens thickness, and both of the rods diverge, past the first bend, towards the optical lens posterior surface. The second bend is located coplanarly with the optical lens itself, while the rod ends face each other (cf. USSR Inventor's Certificate No. 1,116,572, Int.Cl. A61F 1/16, 1985).

A disadvantage inherent in the aforesaid known intraocular lens resides in the fact that holding of the loop-shaped supporting element involves the provision of a capsular duplicature, i.e., the lens is implantable only after extracapsular cataract extraction, since the absence of the posterior lenticular capsule and the capsular duplicature results in dislocation of the intraocular lens into the vitreous body.

SUMMARY OF THE INVENTION

The invention is aimed at the provision of an intraocular prosthetic lens which would lend itself to be fixed reliably in the posterior eye chamber after intracapsular cataract extraction.

The object of the invention is accomplished due to the fact that an intraocular prosthetic lens, comprising an optical lens, a first supporting element, bent into a loop shape, and a second supporting element arranged diametrically opposite with respect to the first one and made up of two rods, each of said rods having a first bend spaced somewhat apart from the lens anterior surface and so made that the diverging rods are facing the lens posterior surface, and a second bend coplanar with the lens principal plane and so made that the rod ends are facing each other, according to the invention comprises a third supporting element made up of two rods located on the side of the first supporting element on the same lens surface that mounts the second supporting element, while each of the rods of the third supporting element has a bend which is spaced apart from the lens anterior surface a distance 1.5 to 2 times the lens thickness on the area where the third supporting element is held, said bend being so made that the rods diverge from each other and are parallel to the lens principal plane and to the first supporting element.

BRIEF DESCRIPTION OF THE DRAWINGS

The foregoing and other objects will become more apparent from a consideration of a detailed description of the present invention with reference to the accompanying drawings, wherein:

FIG. 1 is a front view of the intraocular prosthetic lens, according to the invention;

FIG. 2 is a side view of FIG. 1;

DETAILED DESCRIPTION OF THE INVENTION

Figure 3:
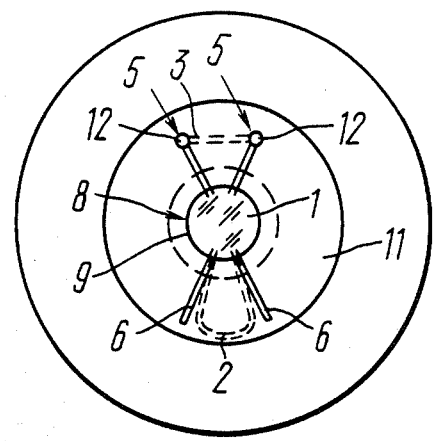
FIG. 3 is a front view of the intraocular prosthetic lens when implanted in an ocular chamber, according to the invention.

The intraocular prosthetic lens comprises an optical lens 1 (FIGS. 1, 2) provided with a bottom supporting element made as a loop 2.

Arranged diametrically opposite to the bottom supporting element is a top supporting element having two rods 3 each provided with bends 4 and 5. Each of the rods 3 is held to the lens 1 at the edge of its optical portion square with the principal plane of the lens 1. The first bend 4 is spaced apart from the anterior surface of the lens 1 a distance 1.5 times the lens thickness, while the rods 3 diverge, past the first bend, towards the posterior surface of the lens 1, and the second bend 5 is coplanar with the lens 1, while the ends of the rods 3 are facing each other.

The intraocular prosthetic lens has a third supporting element made up of two rods 6 located on the lens 1 on its side facing the loop 2 and on the same lens surface that mounts the rods 3. The rods 6 has a bend 7 so made that the rods 6 diverge from each other as can be seen from FIG. 1, while remaining parallel to the loop 2 in the plane of the lens 1 as is shown in FIG. 2.

The bends 7 on each of the rods 6 and the bend 4 on the rods 3 are spaced apart from the front surface of the lens 1 a distance 'h' which is 1.5 to 2 times the lens thickness 'b' on its section where the rods 6 are held.

When the distance 'h' is less than 1.5b, this will results in a traumatic lesion inflicted upon the iris during implantation, since the iris should be interposed between the rods 6 and the loop 2. When the distance 'h' exceeds 2b, the corneal endothelium will be injured by the rods 6.

The following values of 'h' and 'b' are assumed to be the most practicable: h=0.7 mm; b=0.4 mm. All the supporting elements are held in place to the lens 1.

The intraocular lens implantation technique is as follows.

Figure 4:
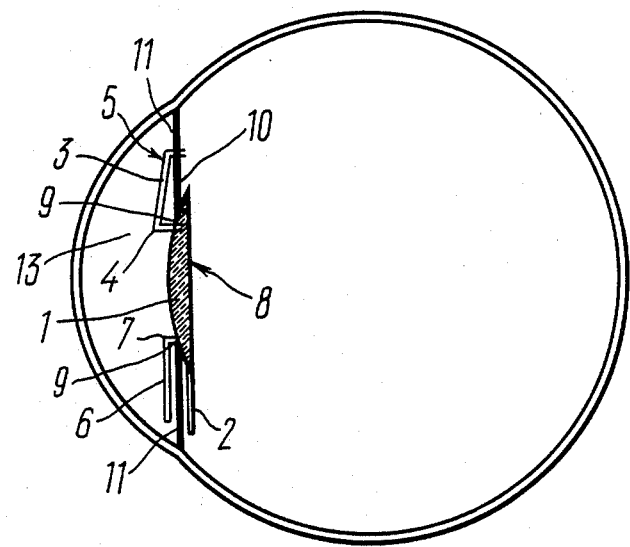
FIG. 4 is a side view of the intraocular prosthetic lens when implanted in an ocular chamber, according to the invention.

Once the cataract has been extracted extracapsularly (with the posterior lenticular capsule remaining intact)

or intracapsularly (together with the lenticular capsule), an intraocular prosthetic lens 8 (FIGS. 3, 4) is brought into a posterior eye chamber 10 through a pupil 9. In this case the loop 2 is placed behind an iris 11, and both of the rods 3 are arranged in front of the iris 11. The first bend 4 on the rods 3 is situated on the margin of the pupil 9, while the second bend 5 is arranged coplanarly with the iris 11. The ends of the rods 3 are passed behind the iris 11 through two punctuate holes 12 made therein.

The rods 6 are so located anteriorly of the iris 11 that their segment confined within the surface of the lens 1 and the bend 7 contacts the pupillary margin 9 of the iris 11.

The intraocular prosthetic lens 8 differs from a heretofore-known one in having a stepped profile, i.e., the first bend on the rods 3 and 6 is spaced 0.4 to 0.7 mm apart from the anterior surface of the lens 1. That portion of the intraocular lens 8 which is accommodated in the posterior eye chamber 10 (i.e., the optical lens 1 and the loop 2), is as short as 7 mm which enables one to implant the intraocular lens 8 through a natural opening, that is, the pupil 9. Since a distance from the radix of the iris 11 to the opposite margin of the pupil 9 equals approximately 7 mm in human's eye, this renders an additional incision of the iris 11 no longer necessary and thus precludes any further injury to the eye operated upon, as well as simplifies the implantation technique and cuts down the operating time, as suturing of the incision into the iris 11 can be dispensed with.

The rods 3 located in an anterior eye chamber 13, hold the lens 1 by passing their ends through the punctuate holes 12 in the iris 11 as far as the bend 5. In addition, the rods 6 which are also accommodated in the anterior eye chamber 13, keep the lens 1 in position within the posterior eye chamber by fixing the rods 6 in the place where the bend 7 is located on the pupillary margin and the rods 6 contact the anterior surface of the iris 11.

While comparing the results of application of a heretofore-known intraocular prosthetic lens with those of the proposed lens, it is quite obvious that a positive effect obtained from application of the novel intraocular prosthetic lens consists in the following: there is provided reliably holding of the posterior-chamber intraocular lens subsequent to cataract extraction by any technique.

What is claimed is:

1. An intraocular prosthetic lens, comprising:
   an optical lens having a principal plane, an anterior surface and a posterior surface;
   a first supporting element secured on said optical lens and bent into a loop shape;
   a second supporting element secured on said optical lens diametrically opposite to said first supporting element and provided with a first and a second rod;
   a first bend is made on said first and said second rods a distance from said anterior surface of said optical lens, said first rod and said second rod diverging, past said first bend, from each other towards said posterior surface of said optical lens; a second bend is provided on said first and said second rods, lying in said principal plane of said optical lens, the ends of said first and said second rods being directed, past said second bend, towards each other;
   said optical lens having a portion for said first supporting element to hold; a third supporting element secured on said portion for holding said optical lens and having a third and a fourth rod located on said optical lens on the side facing said first supporting element and on the same surface of said optical lens with said second supporting element; said third and said fourth rods having a bend past which said third and said fourth rods diverge from each other and are arranged parallel to said principal plane of said optical lens and to said first supporting element; said bend on said third and said fourth rods being spaced apart from said anterior surface of said optical lens a distance which is 1.5 to 2 times the thickness of said optical lens on said portion thereof for said first and said second supporting elements to hold.

* * * * *